US005368544A

United States Patent [19]
Tran et al.

[11] Patent Number: 5,368,544
[45] Date of Patent: Nov. 29, 1994

[54] TREATMENT OF LIVING BODIES

[75] Inventors: Tony N. T. Tran; Van N. Pham, both of Abbotsford, Australia

[73] Assignee: TN Bio-Electronics Pty. Ltd., Australia

[21] Appl. No.: 856,160

[22] PCT Filed: Oct. 16, 1991

[86] PCT No.: PCT/AU90/00476
§ 371 Date: Apr. 1, 1992
§ 102(e) Date: Apr. 1, 1992

[87] PCT Pub. No.: WO91/04764
PCT Pub. Date: Apr. 18, 1991

[30] Foreign Application Priority Data
Oct. 5, 1990 [AU] Australia ............... PJ6726

[51] Int. Cl.$^5$ ............................................. A61B 17/52
[52] U.S. Cl. ........................................... 600/9; 607/65
[58] Field of Search ................................... 600/9–15;
128/420.5, 421, 424; 607/65–76

[56] References Cited
U.S. PATENT DOCUMENTS 4,233,965 11/1980 Fairbanks .
4,911,686 3/1990 Thaler .................................. 600/14
4,998,913 3/1991 Atwood, Jr. ....................... 600/14

FOREIGN PATENT DOCUMENTS
3517874 11/1986 Germany .
1-124474 5/1989 Japan .

Primary Examiner—Lee S. Cohen
Assistant Examiner—J. P. Lacyk
Attorney, Agent, or Firm—Larson and Taylor

[57] ABSTRACT

A method and apparatus is provided for electrically stimulating magnetotherapy to a living body. The apparatus comprises a permanent magnet and a coil of D-block transition metal surrounding the permanent magnet. A voltage is applied across the coil in a direction to enhance the magnetic flux in the permanent magnet. The negative charge of these free electrons is thought to attract the positive electromagnetic charge of the enhanced magnetic flux so a magnetic flux can be electromagnetically transferred with the electron flow through the permanent magnet and conductors through the terminals to enable the magnetic flux to pass to and through the living body. The circuit has an output circuit which will assist the flow of the magnetic flux through the living body. The output circuit has two coils which boost the magnetic flux to thereby assist the flow of the magnetic flux.

22 Claims, 5 Drawing Sheets 5,368,544

TREATMENT OF LIVING BODIES

FIELD OF THE INVENTION

This invention relates to treatment of living bodies and relates particularly, but not exclusively, to treatment of the human body.

DESCRIPTION OF PRIOR ART

It has been well known and well documented that magnetotherapy can improve certain conditions in human bodies. This therapy is thousands of years old but recent work by Dr. Jean-Bernard Baron of National Scientific Research Centre in Paris, France has documented that considerable improvement can be achieved in connection with a wide range of disorders including convergence of the eye, scoliosis, hemiphlegia, facial paralysis, muscle contractures, arthritis, tendonitis, synovitis, tension headache, post-operative and other pain, and sports injuries.

As a result of the research by Dr. J-B. Baron, other doctors in different medical research institutions have followed him in studying the healing effects provided by magnetotherapy. Similar works have been undertaken in Japan but no scientific materials have been published.

The practice of magnetotherapy involves applying small permanent magnets across the affected areas so that a flux will flow into the human body. Many devices have been created for applying the flux of the permanent magnets to the body. One recent innovation involves the use of permanent magnets embedded within a blanket upon which a patient lies or which is placed over the patient. Contact is made with the affected area so that flux can flow into the body.

OBJECT AND STATEMENT OF THE INVENTION

The application of permanent magnets directly to the skin of the human body across the affected area is considered to be generally unpleasant and partly troublesome to implement. In the case of the magnetic blankets, good magnetic contact with the surface of the skin across the affected area is not always possible. Accordingly, enhanced treatment could be provided if the magnetic flux could be applied electrically to the human body across the affected area. Accordingly it is an object of the present invention to provide a method and apparatus for electrically simulating the treatment which can be produced by magnetotherapy.

We have ascertained that a magnetic flux can be carried in a conductor by the electrons in the conductor provided the conductor itself is of a type which has free electrons.

Accordingly, with the above in mind, a first broad aspect of the present invention may reside in a method of treating a living body for the purpose of simulating the treatment which can be produced by magnetotherapy comprising:

(a) providing a permanent magnet within an electrical coil of a D-block transition metal;

(b) passing a current through said coil in a direction which will enhance the magnetic flux of said permanent magnet;

(c) applying conductors of a D-block transition metal to said coil and across an area to be treated on the living body; and (d) allowing a further current to flow through said conductors through the living body to cause a magnetic flux to pass through the living body.

It may also be said that a further broad aspect of the present invention relates to apparatus for treating a living body for simulating the treatment which can be provided by magnetotherapy comprising:

electrical circuit means having a coil of a D-block transition metal, a permanent magnet mounted within said coil, and conductors of a D-block transition metal connectable with said coil and being for application to the living body, electrical power providing means within said circuit means for permitting a current to flow through said coil in a direction to enhance the magnetic flux in said coil and to simultaneously permit a further current to flow through said conductors and through said living body when connected with said conductors whereby a magnetic flux can be provided in said conductors and passed through the living body.

Most preferably, said electric circuit means contains electric accelerating means for accelerating electrons carrying said further current.

It is particularly preferred that the apparatus be battery driven, and that the battery be rechargeable from mains AC power.

BRIEF DESCRIPTION OF DRAWINGS

In order that the invention can be more clearly ascertained, an example of a preferred embodiment will now be described with reference to the accompanying drawings, wherein.

DESCRIPTION OF PREFERRED EMBODIMENT

Figure 1:
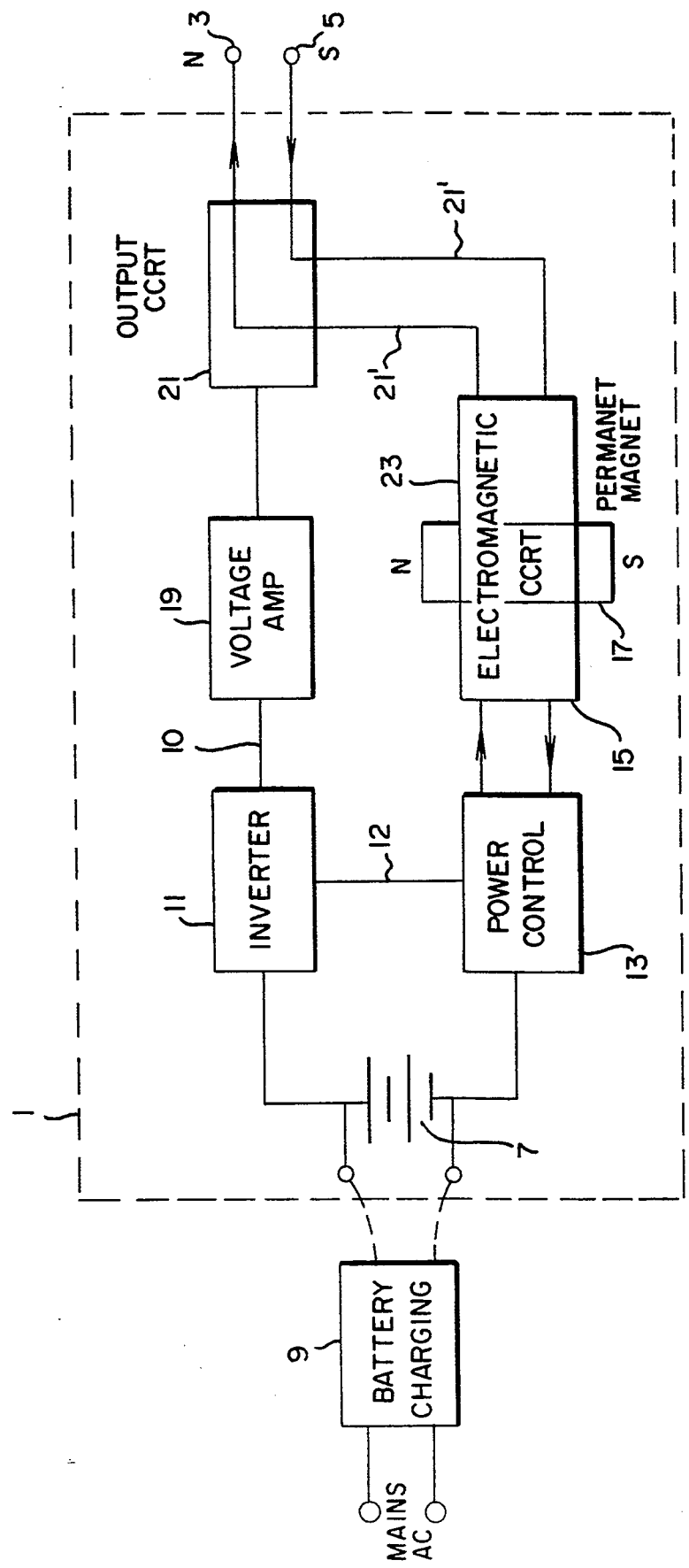
FIG. 1 is a block schematic circuit diagram of an example of the preferred apparatus.

Referring now to FIG. 1 there is shown a block schematic circuit diagram of the example of the preferred apparatus. Here it can be seen there is provided a main circuit 1 which has a pair of output terminals 3 and 5. Output terminal 3 can be considered a north magnetic pole and output terminal 5 can be considered a south magnetic pole. In use, current will flow along conductor means which is connected with the terminals 3 and 5 to cause a current to flow into the living body such as a human body. The current will carry magnetic flux as will be explained hereinafter.

The main circuit 1 is powered by a battery 7. The battery 7 is preferably rechargeable from a battery charging circuit 9 which is connectable with mains AC power.

Within the main circuit 1 is provided an inverter circuit 11 for producing two voltage outputs 10 and 12, a power control circuit 13, an electromagnetic circuit 15, a permanent magnet 17, a voltage amplifier circuit 19 and an output circuit 21.

The electromagnetic circuit 15 contains a coil 23 of a D-block transition metal. The coil 23 is sufficiently large to receive a permanent magnet 17 therethrough. When power is applied to the electromagnetic circuit 15 from the power control circuit 13, it causes a current to flow through the coil 23 in a direction which will enhance the magnetic flux in the permanent magnet 17. Conductors 21' of a D-block transition metal electrically connect with the coil in the electromagnetic circuit 15.

The following theory is thought to be applicable as to how the magnetic flux can transfer from the permanent magnet 23 in the electromagnetic circuit 15 to the conductors 21. The magnetic particles within the permanent magnet 17 are basically orientated in one direction in order that the permanent magnet will have a north and south pole. The orientation is not complete as all the particles do not align themselves in parallel but merely in a general direction such that there will be a north and a south pole predominating. Application of the current to the coil 23 in the electromagnetic circuit 15 is in a direction which will enhance the magnetic flux in the permanent magnet 23. This, in turn, creates an intensive electromagnet flux in the permanent magnet 17 which will have a positive electromagnetic charge. The D-block transition metal from which the coil is made is within the magnetic flux which is now highly and intensely concentrated to be directed between the north and south poles of the permanent magnet. The D-block transition metal from which the coil 23 is made is characterized by having paired electrons which are readily free. These electrons have a negative atomic charge and are attracted to the positive electromagnetic charge created by the intense magnetic flux. Thus, the paired electrons, because of their attraction to the positive electromagnetic charge, will carry the attracted positive electromagnetic charge as the electrons flow through the conductor. In addition a current flows directly through the permanent magnet and such current carries with it a magnetic flux from the intensified flux in the permanent magnet. Thus, the current flowing through coil 27 and through permanent magnet are combined to produce a current carrying the magnetic flux. This, in turn, is thought to permit the magnetic flux associated with the positive electromagnetic charge to be transferred with the electrons through the conductors. Thus, a magnetic flux which is not normally considered to be carriable by an electrical current can be carried with the electron flow associated with the current passing through the conductors 21. Because the conductors which connect with the terminals 3 and 5 are also of a D-block transition metal, the magnetic flux which is attracted to the negative electrons will flow through the conductors and into the human body. Thus, as a current flows across the terminals 3 and 5 it will carry the magnetic flux with it like that of a carrier modulated with the flux pulses. The magnetic flux will therefore pass into the human body with the carrier current.

The D-block transition metal can be said to have loose paired electrons at the outer shell (which is said D-orbital). This renders such metals oxiditic over wide ranges of states. Such metals are dense and high melting and exhibit very high thermal and electrical conductivity and are therefore able to carry the magnetic flux in a condensed and uniform state.

The voltage amplifier 19 provides a high potential which is applied to an output circuit 21. The output circuit 21 does not electrically connect with the conductors 21 but merely provides a high potential in proximity to the conductors 21 to accelerate the free electrons flowing in the conductors 21 to, in turn, assist in boosting the flow of the electrons carrying the magnetic flux across terminals 3 and 5. The output circuit 21 can conveniently comprise a respective coil for each of the conductors 21. Thus, one of the coils can be used to accelerate the electrons passing from the apparatus whilst the other coil can be used to accelerate the electrons returning to the apparatus.

It is thought that the magnetic flux is carried into the human body by polar attraction. In other words, it is attracted by the negative ions and the negative polar molecules within the body which are present in water which comprises a major component of the human body. Water has a particular molecular structure in that the shared electron pairs within water causes the molecule to have a V-shape. The unshared electron pairs of each oxygen atom within the water give it a localized partial negative charge at the apex of the V. This negative charge of water attracts the north electromagnetic flux and the body is filled with the magnetic flux which flows.

Figure 2A:
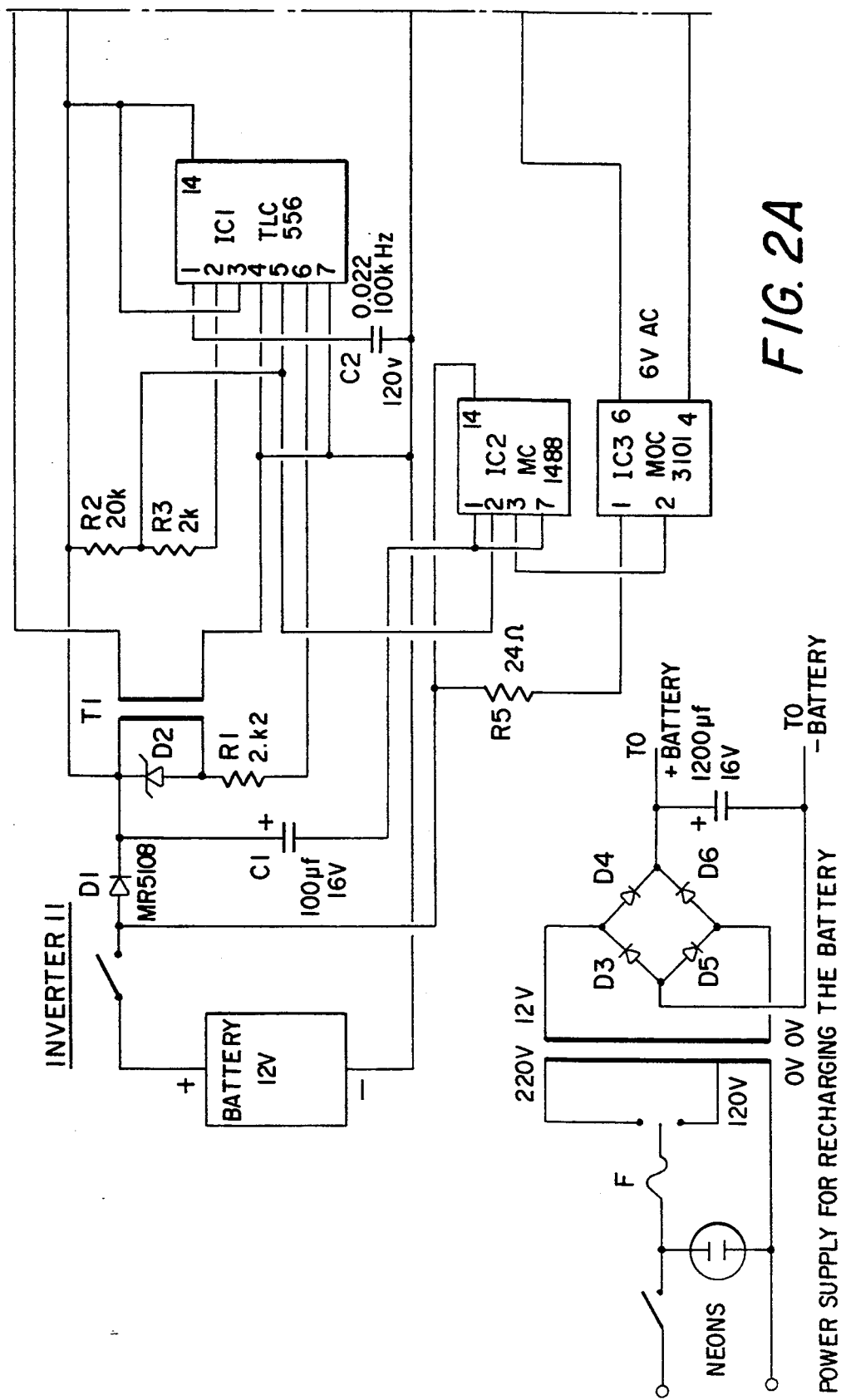
FIGS. 2A and 2B are detailed circuit diagrams of the apparatus shown in FIG. 1.
Figure 2B:
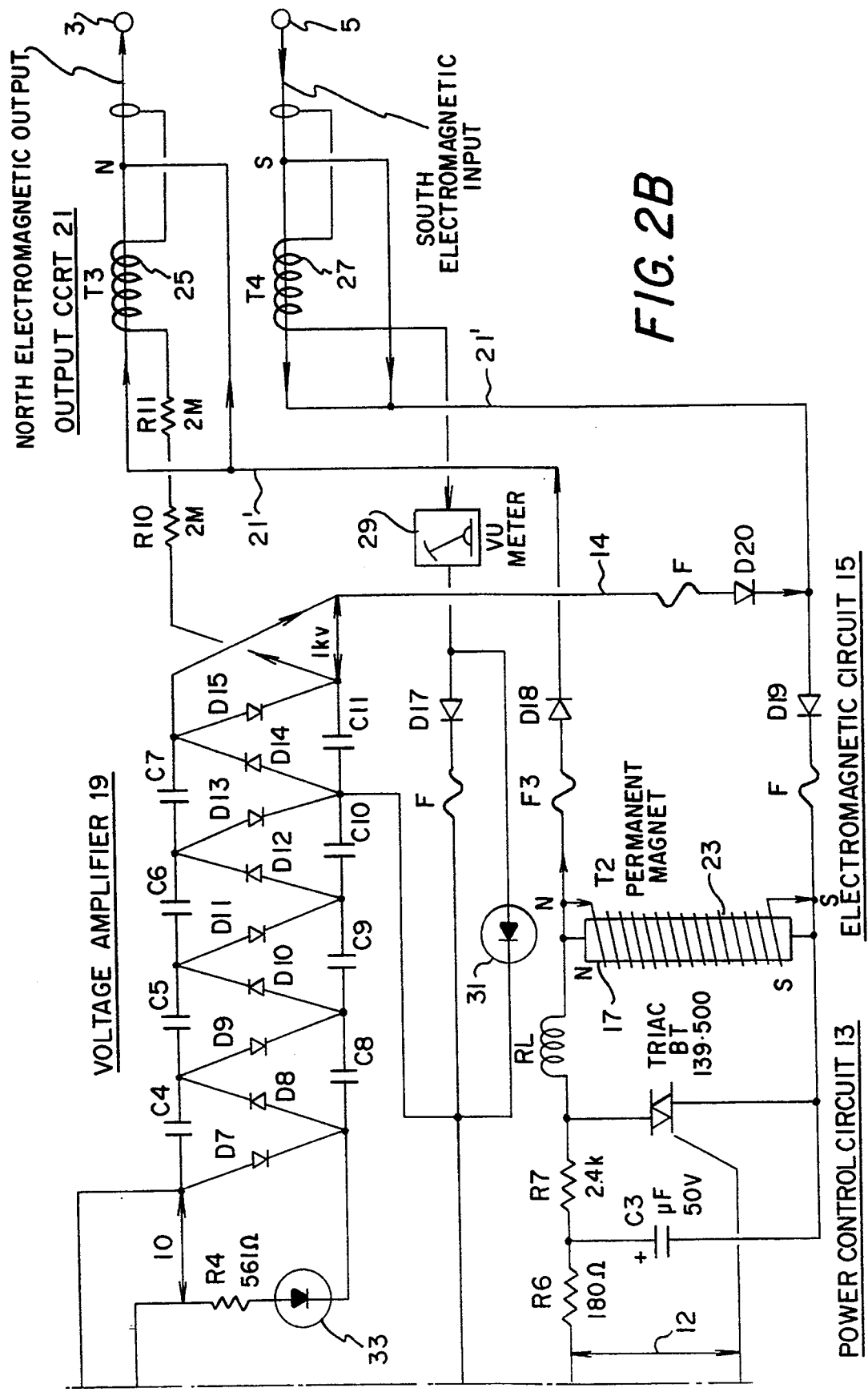

Referring now to FIGS. 2A and 2B there is shown a detailed circuit diagram of the apparatus shown in FIG. 1.

The circuit is basically self-explanatory. Here it can be seen that the inverter circuit provides two output voltages 10 and 12. The first output voltage 12 of 6 volts AC of 24 Hertz is half wave rectified and applied across a coil 23 in the electromagnetic circuit 15. The current flow can be approximately half an amp. Typically the coil 23 comprises a copper coil having ten turns wound over the permanent magnet 17. Typically the magnet has a flux density of approximately 15 webbers and comprises a ferrite of 10 mm diameter and of 30 mm length. The second output voltage 10 of the inverter circuit 11 is applied to the voltage amplifier circuit through a series of diodes D7-D15 to provide about a 1kV pulsed DC output in a range of 20K Hertz to 500K Hertz and preferably at 100K Hertz. The pulsing is in a range of 2 Hertz to 1K Hertz and preferably at 24 Hertz and occurs by circuit conductor 14 connecting between the output of diodes D7-D15 and the first output voltage 12. This pulsed output is applied to the output circuit 21' to respective coils 25 and 27. The coils have an ionic air return electrical circuit. Thus, the high voltage appearing from the voltage amplifier circuit 19 is applied to coil 25 with one polarity and to the coil 27 with the opposite polarity. These coils 25 and 27, in turn, place the conductors 21' in proximity to a field created by a high potential which, in turn, is thought to accelerate the free electrons in the conductors 21' to, in turn, boost the flow of magnetic flux which flows from the terminals 3 and 5. Typically, coils 25 and 27 each comprise fifteen turns of copper of 6 mm diameter through which conductors 21' pass. The potential created by coil 25 will assist the flow of magnetic flux passing from the apparatus whilst the potential of coil 27 will assist the flow of flux returning to the apparatus.

Figure 3:
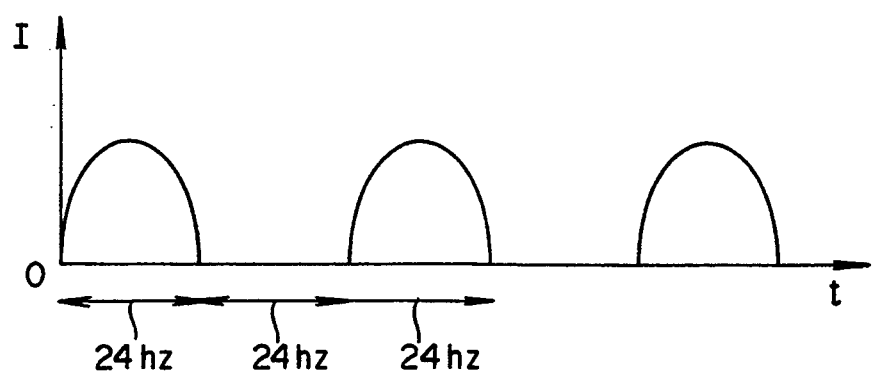
FIGS. 3, 4 and 5 are graphs showing waveforms provided in the apparatus.

FIG. 3 shows a graph of current-v-time showing the half wave 24 Hertz current which is applied across coil 23.

Figure 4:
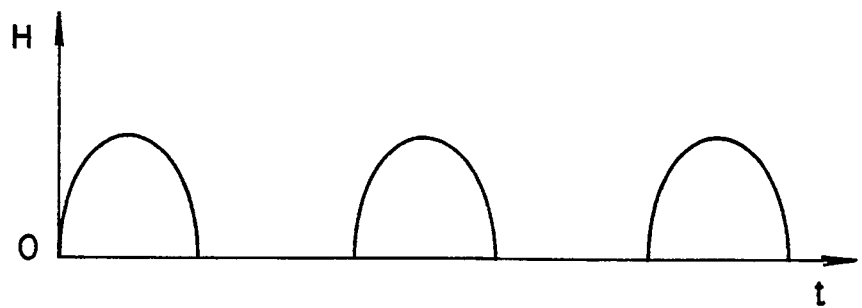

FIG. 4 shows a graph of magnetic flux H-v-time showing the flux which is carried in the conductor of coil 23 as a result of the current being applied to coil 23 as shown in FIG. 3. The flux is therefore pulsed and is thought to be carried by the free electron pairs in the conductor coil 23 as explained previously.

Figure 5:
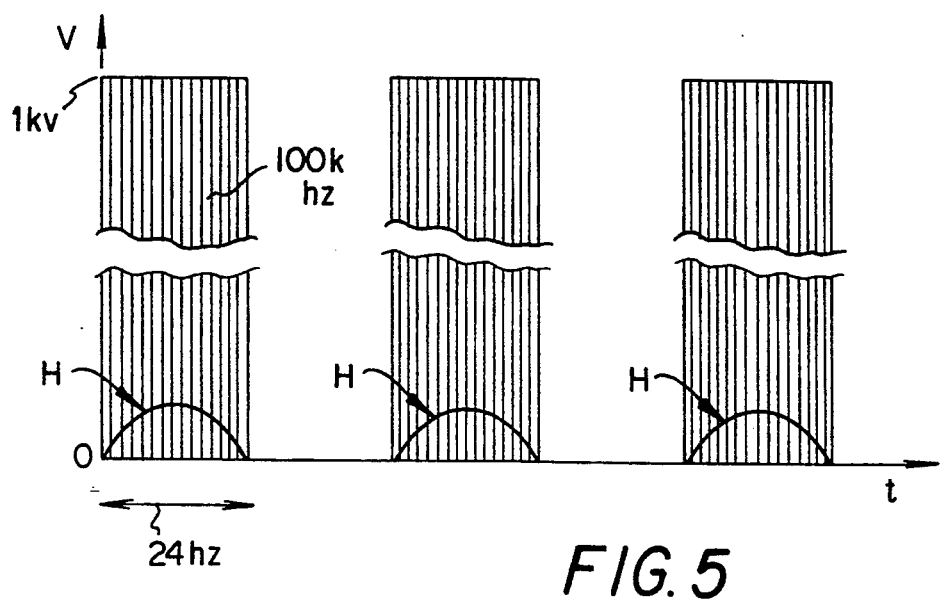

FIG. 5 shows a graph of voltage-v-time showing the application of a 1 kV half wave 100K Hertz pulsed signal across coils 25 and 27. The flux pulses shown in FIG. 4 have been simulated on this graph to show that 1 kV pulses are in phased relationship therewith and pulsed at the same rate—24 Hertz. The effect of this is to produce a flux flowing in the electrodes and through the living body which is pulsed in the range 1K Hertz to 24K Hertz.

A meter 29 and neons 31 are provided to give an indication of voltage and current flow. An LED 33 is provided in the voltage amplifier circuit 19 to indicate current flow into the voltage amplifier circuit 19. The current flow into the living body (patient) is in the order of 10 micro A to 5000 micro A. The magnetic flux at the electrodes is in the order of 10 micro gauss to 7000 micro gauss.

Typically the apparatus is connected with the living body (patient) by connecting copper electrodes with the terminals 3 and 5 and connecting those electrodes across the affected area of the living body. The electrodes must also be of the D-block transition metal in order to permit the required electron flow, hence they are of copper in one example of a D-block transition metal. The patient is treated for periods of time which have been found satisfactory during prior experimentation for similar treatments. Typically a period of approximately ten minutes is employed.

Figure 6:
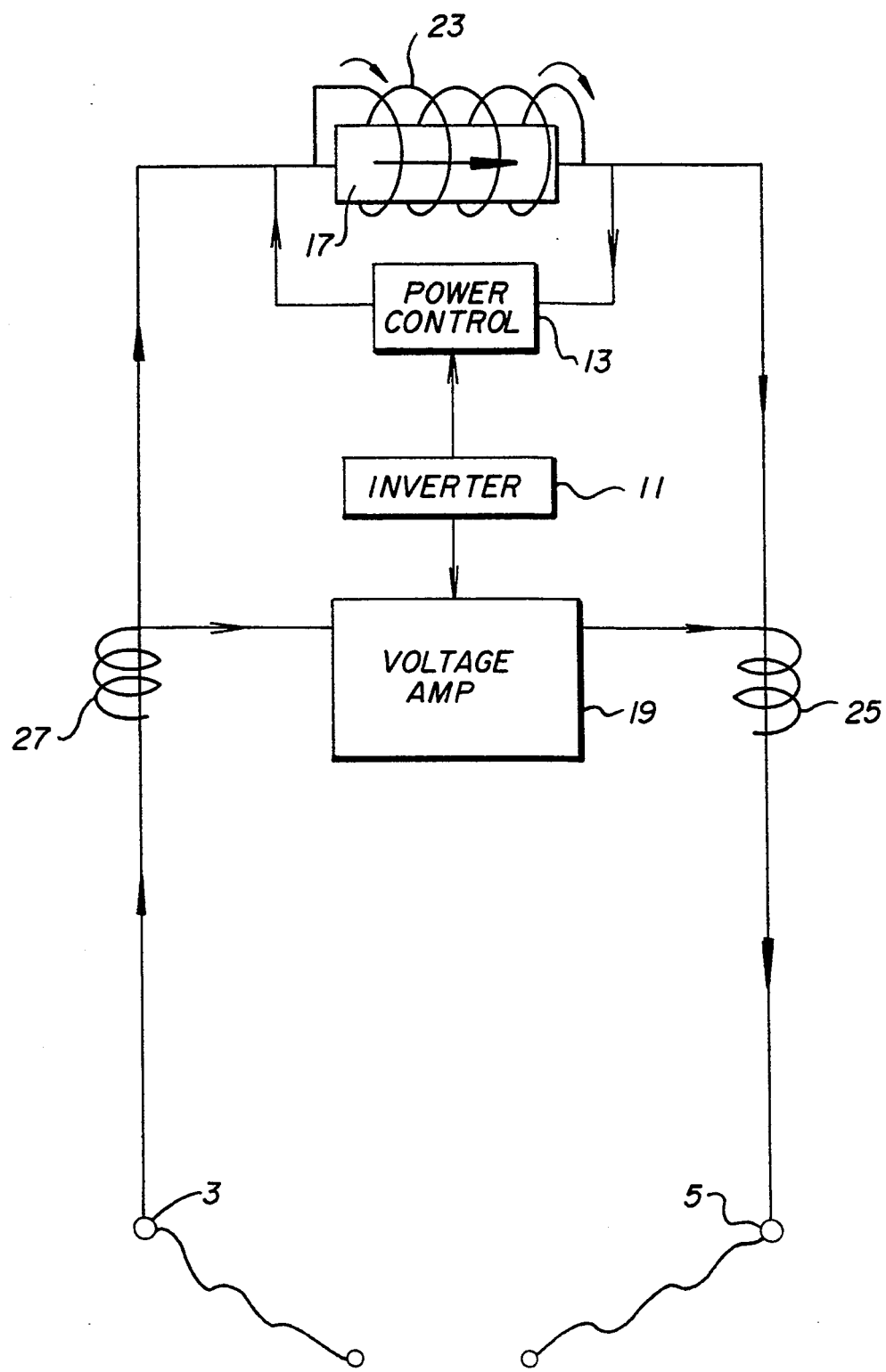
FIG. 6 is a block schematic circuit diagram of the apparatus shown in FIGS. 1-2 showing current flow.

FIG. 6 is a block schematic diagram showing current flow from the inverter 11 to the power control circuit 13, through permanent magnet 17 and through coil 23, and from terminal 5, through a living body back to the apparatus via terminal 3. Current also flows from inverter 11 to the voltage amp 19 to drive the coils 25 and 27 to boost the flux flowing with the current. Thus, FIG. 6 shows not only the current flow but also the flux flow out from terminal 5, and the flux returning through terminal 3.

Modifications may be made to the present invention as would be apparent to persons skilled in the art of treating patients and by those skilled in the art of producing electrical apparatus for treating living bodies.

These and other modifications may be made without departing from the ambit of the invention, the nature of which is to be determined from the foregoing description.

We claim:

1. A method of treating a living body for the purpose of simulating the treatment which can be produced by magnetotherapy comprising:
   (a) providing a permanent magnet within an electrical coil of a D-block transition metal;
   (b) applying conductors of a D-block transition metal to said coil and said permanent magnet and across an area to be treated on the living body;
   (c) passing currents through said coil and said permanent magnet in a direction which will enhance the magnetic flux of said permanent magnet; and
   (d) allowing current to flow through said conductors through the living body to allow a magnetic flux from said permanent magnet to pass through the living body.

2. A method as claimed in claim 1 comprising the further step of pulsing the current through the coil at step (c).

3. A method as claimed in claim 2 wherein the pulsing of the current through the coil is in the range 2 Hertz to 1K Hertz.

4. A method as claimed in claim 3 wherein the pulsing is at about substantially 24 Hertz.

5. A method as claimed in claim 1 comprising the further step of subjecting the conductors at step (b) to a field created by a voltage potential to assist the flow of magnetic flux through the living body.

6. A method as claimed in claim 5 wherein the pulsing of the voltage is in the range of 20K Hertz to 500K Hertz.

7. A method as claimed in claim 6 wherein the pulsing of the voltage is to about substantially 100K Hertz.

8. Apparatus for treating a living body for simulating the treatment which can be provided by magnetotherapy comprising:
   a coil of a D-block transition metal, a permanent magnet having a magnetic flux mounted within said coil, and conductors of a D-block transition metal connected with said coil and with said permanent magnet, said conductors being adapted for application to the living body, electrical power providing means for permitting current to flow through said coil and said permanent magnet in a direction to enhance the magnetic flux and to simultaneously permit current to flow through said conductors and through said living body when connected with said conductors to allow a magnetic flux from said permanent magnet to pass through the living body.

9. Apparatus as claimed in claim 8 including pulsing circuit means for pulsing the current through said coil.

10. Apparatus as claimed in claim 9 wherein said pulsing circuit means comprises an oscillator for providing an AC voltage and rectifier means for permitting voltage pulses from said AC voltage to be provided so the current through said coil can be pulsed.

11. Apparatus as claimed in claim 10 wherein said oscillator provides an AC output voltage in the range 2 Hertz to 1K Hertz.

12. Apparatus as claimed in claim 11 wherein said oscillator and said rectifier means provides about substantially 24 Hertz voltage output pulses.

13. Apparatus as claimed in claim 10 wherein said conductors are, in use, subjected to a field created by a voltage potential to assist the flow of magnetic flux through the living body; including further oscillator circuit and rectifier means for providing said voltage potential.

14. Apparatus as claimed in claim 13 wherein said further oscillator circuit and rectifier means provides voltage pulsed in the range of 20K Hertz to 500K Hertz.

15. Apparatus as claimed in claim 14 wherein said further oscillator circuit and rectifier means provides voltage pulsed at about substantially 100K Hertz.

16. Apparatus as claimed in claim 15 wherein the voltage is about substantially 1 kV.

17. Apparatus as claimed in claim 13 further including a first further coil and a second further coil; wherein said voltage is applied to said first further coil which surrounds an output conductor of said conductors and to said second further coil which surrounds a return conductor of said conductors.

18. Apparatus as claimed in claim 17 wherein each of said coils has an ionic air return circuit.

19. Apparatus as claimed in claim 10 wherein the D-block transition metal is copper.

20. Apparatus as claimed in claim 8 wherein the current flow into the living body is in the order of 10 micro amp to 5000 micro amp.

21. Apparatus as claimed in claim 8 wherein the magnetic flux which passes through the living body is in the order of 10 micro gauss to 7000 micro gauss.

22. Apparatus as claimed in claim 9 wherein the magnetic flux which passes into the living body is pulsed in the order of about 1K Hertz to 24K Hertz.

* * * * *